United States Patent [19]

Webber

[11] 4,065,620
[45] Dec. 27, 1977

[54] 3-(SUBSTITUTED) VINYL CEPHALOSPORINS

[75] Inventor: John Alan Webber, Indianapolis, Ind.

[73] Assignee: Eli Lilly and Company, Indianapolis, Ind.

[21] Appl. No.: 153,065

[22] Filed: June 14, 1971

[51] Int. Cl.$^2$ .................. C07D 501/18; C07D 501/20
[52] U.S. Cl. .................................... 544/16; 424/246
[58] Field of Search .................................. 260/243 C

[56] References Cited

U.S. PATENT DOCUMENTS

| | | |
|---|---|---|
| 3,660,396 | 5/1972 | Wright .............................. 260/243 C |
| 3,674,784 | 7/1972 | Webber ............................ 260/243 C |
| 3,682,903 | 8/1972 | Bickel et al. .................... 260/243 C |
| 3,769,277 | 10/1973 | Long et al. ...................... 260/243 C |
| 3,994,884 | 11/1976 | Weir ................................ 260/243 C |

Primary Examiner—Nicholas S. Rizzo
Attorney, Agent, or Firm—William B. Scanlon; Everet F. Smith

[57] ABSTRACT

New 3-(substituted) vinyl cephalosporin compounds, e.g., 3-(2'-ethoxycarbonylvinyl)-7-phenoxyacetamido-3-cephem-4-carboxylic acid, which are useful as antibiotics, and 3-(substituted) vinyl cephalosporin compounds which are useful as intermediates in preparing antibiotic substances.

18 Claims, No Drawings

3-(SUBSTITUTED) VINYL CEPHALOSPORINS

INTRODUCTION

This invention relates to cephalosporin compounds which are useful as antibiotics or as intermediates in processes for preparing antibiotic substances.

BACKGROUND OF THE INVENTION a. General Cephalosporin History.

Cephalosporin C, obtained by fermentation, has been defined as having the following structure:

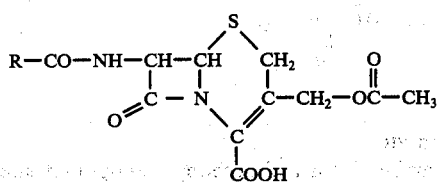
(I)

where R is $HOOC-CH(NH_2)-(CH_2)_3-$. It is also known as 7-(5'-aminoadipamido)cephalosporanic acid. It has weak antibiotic activity, but it is important as a source of cephalosporin C nucleus, i.e., 7-aminocephalosporanic acid (7-ACA), having the structural formula

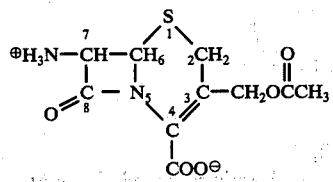
(II)

shown here in zwitterionic form, although anionic and cationic salts may be formed and used. Antibiotics such as cephalothin and cephaloridine are prepared from 7-ACA by known methods. Various derivatives of 7-ACA based antibiotics are made by acylating the 7-amino group of 7-ACA with appropriate acyl acids, halides, or other reactive form of such acyl groups and/or by replacing the acetoxy group attached to the 3-methyl carbon atom with appropriate nucleophilic groups now well documented in the literature.

In continued research, desacetoxycephalosporin compounds, i.e., compounds of the structure

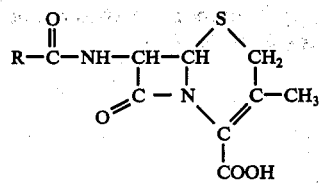
(III)

where R is the residue of the acyl group have been prepared. An important known antibiotically active compound in this class is cephalexin, an orally active cephalosporin antibiotic. Morin and Jackson (U.S. Pat. No. 3,275,626) discovered a process for preparing the desacetoxycephalosporanic acid derivatives by rearranging a penicillin sulfoxide ester to the corresponding desacetoxycephalosporin ester, and then removing the ester group. Desacetoxycephalosporanic acid derivative antibiotics are thus obtainable from a penicillin starting material. The compounds are sometimes, for convenience, referred to as being derivatives of 7-aminodesacetoxycephalosporanic acid (7-ADCA) having the structure

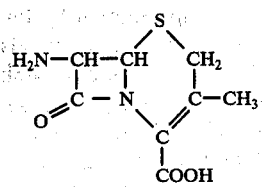
(IV)

b. 3-Formyl Cephalosporin Prior Art

In U.S. Pat. No. 3,351,596, issued Nov. 7, 1967, James W. Chamberlin disclosed and claimed a process for preparing 3-formylcephalosporin esters comprising the reaction of a 3-hydroxymethyl-7-acylamido-3-cephem-4-carboxylic acid compound with a diazo compound to obtain the ester, and then reacting that ester with an oxidizing agent selected from the group consisting of manganese dioxide and chromium trioxide. The products of that reaction are 3-formylcephalosporin esters having the sulfur in the 1-position in the bivalent or sulfide state. In my prior application Ser. No. 58,678, filed July 27, 1970, now U.S. Pat. No. 3,674,784, I have claimed some new 3-formyl cephalosporin sulfoxide esters and have described a process for making them. Such 3-formyl cephalosporin sulfoxide as well as sulfide esters can be used as starting materials in processes for preparing the new 3-(substituted) vinyl cephalosporin compounds of this invention. Briefly, the 3-formyl cephalosporin sulfide or sulfoxide esters can be prepared in good yields by reacting an oxidizing agent with a 3-hydroxymethyl-7-(N-protected amino)-3-cephem-4-carboxylate or its sulfoxide in a substantially anhydrous organic liquid medium which does not interfere with the desired reaction, at temperatures above the freezing point of the mixture to about 50° C. until the 3-formyl-7-(N-protected amino)-3-cephem-4-carboxylate or its sulfoxide is formed.

It is an object of this invention to provide some new cephalosporin compounds which are useful as antibiotics or as intermediates in processes for preparing antibiotics.

It is another but more specific object of this invention to provide some new 3-(substituted) vinyl cephalosporin compounds which are useful generally as antibacterial agents and some of which are of particular interest because of their activity against *Serratia marcescens* and *Pseudomonas aeruginosa*, indole-positive Proteus strains and Enterobacter species.

Other objects, aspects, and advantages of the invention will become apparent from reading the remainder of the specification which follows.

SUMMARY OF THE INVENTION

According to this invention, I have discovered new cephalosporin compounds having a substituted vinyl group bonded to the carbon atom in the 3-position of the cephem ring moiety of the cephalosporin compound. For want of a better shorthand term, they are referred to herein as "3-(substituted)vinyl cephalosporin" compounds. The new compounds are prepared by reacting a 3-formyl cephalosporin sulfide or sulfoxide ester with a phosphorane derivative to form the respective 3-(substituted)vinyl cephalosporin sulfide or sulfoxide ester. Included within this invention are the 3-(substituted)vinyl cephalosporin ester sulfoxides, the 3-(substituted)vinyl cephalosporin esters, the 7-amino-3-(substituted) vinyl cephalosporin ester nuclei compounds, acid salts of such compounds, the free acids of any of such compounds after ester group removal by known means, as well as any of such nuclei compounds reacylated with groups known to contribute to cephalosporin compound antibiotic activity. These 7-acylamido-3-(substituted)vinyl cephalosporanic acid compounds of this invention are active against a variety of Gram positive and Gram negative microorganisms. Some of these compounds are of particular interest because they show substantial activity against *Serratia marcescens, Pseudomonas aeruginosa,* Enterobacter type organisms and indole-positive Proteus strains in standard gradient plate assay procedures. Activity in these tests against various organisms has been indicative of antibiotic activity of all of the presently commercial cephalosporin antibiotics, namely, cephalothin, cephaloridine, cephaloglycin, and cephalexin. For example, a new compound of this invention, 7-(2'-carboxy-2'-phenylacetamido)-3-(2'-carboxyvinyl)-3-cephem-4-carboxylic acid, and 7-(2'-carboxy-2'-phenylacetamido)-3-(2'-ethoxycarbonylvinyl)-3-cephem-4-carboxylic acid show significant antibiotic activity against *Pseudomonas aeruginosa* (under 50 micrograms/ml.) in standard gradient plate assays.

DETAILED DESCRIPTION OF THE INVENTION

This invention provides new 3-(substituted)vinyl cephalosporin compounds which may be defined by the structural formula

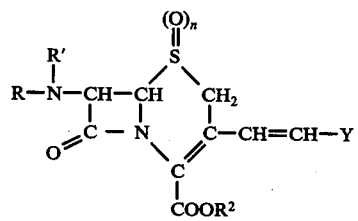

wherein $n$ is 0 or 1,

R is hydrogen, $C_1$ to $C_8$-alkanoyl, $C_2$ to $C_8$-chloro- or bromoalkanoyl, azidoacetyl, cyanoacetyl

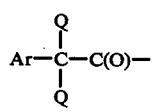

where each Q is hydrogen or methyl, and Ar denotes 2-thienyl, 3-thienyl, 2-furyl, 3-furyl, 2-pyrrolyl, 3-pyrrolyl, phenyl, phenyl substituted with chlorine, bromine, iodine, fluorine, trifluoromethyl, hydroxy, $C_1$ to $C_3$-alkyl, $C_1$ to $C_3$-alkyloxy cyano, or nitro, at least one of such substituents being in the meta or para position of the phenyl ring;

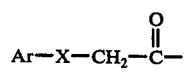

where Ar is as defined above, and X is oxygen or sulfur, or Ar is 4-pyridyl where X is sulfur;

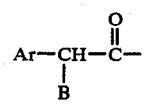

where Ar is as defined above and B denotes —NH$_2$, —NH$_3$+, an amino group protected with a benzyloxycarbonyl, a $C_1$ to $C_4$-alkyloxycarbonyl, cyclopentyloxycarbonyl, cyclohexyloxycarbonyl, benzhydryloxycarbonyl, a triphenylmethyl, 2,2,2-trichloroethoxycarbonyl,

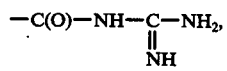

SO$_3$H,
phthalimido,
the enamine from a dicarbonyl compound such as methyl acetoacetate, acetylacetone, and the like; or B is —OH, —COOH, or such groups protected by esterification with $C_1$ to $C_6$-alkanoic acids or $C_1$ to $C_6$-alkanols, respectively, or B is —N$_3$, —CN, or —C(O)NH$_2$;

or R is 2-sydnone-3-$C_1$ to $C_3$-alkanoyl-,

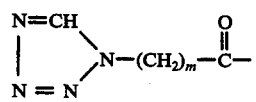

where $m$ is 0 to 2, 5-aminoadipoyl, or 5-aminoadipoyl in which the amino group is protected by acylation with a $C_1$ to $C_3$-alkanoyl, a $C_1$ to $C_3$-chloroalkanoyl, and those aminoadipoyl groups in which the carboxyl groups are protected, e.g., by esterification with an easily cleavable ester, such as benzhydryl, 2,2,2-trichloroethyl, $C_4$ to $C_6$-tert-alkyl, nitrobenzyl, or the like;

R$^1$ is hydrogen, or

R and R$^1$ taken together with the nitrogen to which they are bonded denote H$_3$N+—, a salt group with an acid having a pKa less than 4, such as $C_1$ to $C_{12}$-alkanesulfonic acid, benzenesulfonic acid a $C_1$ to $C_4$ alkylbenzenesulfonic acid, hydrochloric acid, sulfuric acid, or the like, or a cyclic imide group from a $C_3$ to $C_{12}$-hydrocarbon dicarboxylic acid or reactive derivative of such acid;

R$^2$ is $C_4$ to $C_6$-tert alkyl,
$C_5$ to $C_7$-tert alkenyl,
$C_5$ to $C_7$-tert alkynyl,
benzyl,
methoxybenzyl,
nitrobenzyl,
2,2,2-trichloroethyl,
2-iodoethyl,
benzhydryl,
phenacyl,
trimethylsilyl,
succinimidomethyl,
phthalimidomethyl,
hydrogen, or a pharmaceutically acceptable cation;

and Y is —C(O)OR$^3$, where R$^3$ denotes a C$_1$ to C$_4$ alkyl, a methoxybenzyl, nitrobenzyl, benzhydryl (diphenylmethyl) or 2,2,2-trichloroethyl or Y is —CN,
—COOH,
—CHO,
—X-C$_1$ to C$_4$-alkyl or —X-phenyl where X is oxygen or sulfur,
—C(O)-C$_1$ to C$_3$-alkyl or —C(O)phenyl,
—C(O)NH$_2$,
—NO$_2$,
—S(O)-C$_1$ to C$_4$-alkyl,
—S(O)$_2$-C$_1$ to C$_4$-alkyl,
—Cl or -Br,
—CF$_3$,
—C$_1$ to C$_6$-alkyl,
—phenyl,
—phenyl substituted with chlorine, bromine, iodine, —NO$_2$, —CN, —CF$^3$, C$_1$ to C$_4$-alkyl, C$_1$ to C$_4$-alkyl-X-, or —C(X)X-C$_1$ to C$_4$-alkyl where X in each case is oxygen or sulfur, or Y is

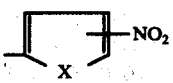

where X is —O— or —S—.

A preferred group of the 3-(substituted)vinyl cephalosporin ester sulfoxides of this invention are those of formula (V) above wherein n is 1; R is Ar-X-CH$_2$-C(O)— where X is —O— and Ar is phenyl, or R is C$_1$ to C$_8$-alkanoyl, R$^1$ is hydrogen; R$^2$ is a C$_4$ to C$_6$-tert-alkyl, benzhydryl, or nitrobenzyl, and Y is —CN, or —COO alkyl having from 1 to 4 carbon atoms in the alkyl groups.

A preferred group of the 3-(substituted)vinyl cephalosporin ester (sulfide) compounds are those of formula (V) above where n is 0; R is C$_1$ to C$_8$-alkanoyl, phenoxyacetyl, phenylacetyl, chloroacetyl, bromoacetyl, 5-aminoadipoyl in which the amino group is protected with a C$_1$ to C$_3$-alkanoyl or C$_1$ to C$_3$-chloroalkanoyl, and the carboxy groups are protected with benzhydryl, 2,2,2-trichloroethyl, C$_4$ to C$_6$-tert-alkyl, or nitrobenzyl, phenyl—CH—C(O)—   or
         |
         Z

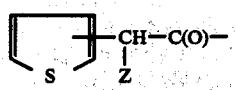

where in each formula Z is hydrogen, —OH, —OH protected by esterification with a C$_1$ to C$_6$-alkanoic acid, —COOH, —COO-alkyl having from 1 to 6 carbon atoms in the alkyl, or Z is —N$_3$, —CN, —C(O)NH$_2$, $$-\overset{H}{NSO_3H}, \text{ or } -NH-C(O)-NH-\underset{\underset{NH}{\|}}{C}-NH_2;$$

R$^1$ is hydrogen;
R$^2$ is C$_4$ to C$_6$-tert-alkyl, benzhydryl or nitrobenzyl, and Y is —CN or —COO alkyl having from 1 to 4 carbon atoms in the alkyl.

A preferred group of 3-(substituted)vinyl cephalosporin ester nuclei compounds are those of formula (V) wherein n is 0, each of R and R$^1$ is hydrogen, R$^2$ is a C$_4$ to C$_6$-tert-alkyl, benzhydryl, or nitrobenzyl; and Y is selected from the group consisting of —CN, —COO-alkyl having from 1 to 4 carbon atoms in each alkyl group, and salts of such compounds with an acid having a pKa of less than 4.

A preferred group of 3-(substituted)vinyl cephalosporin acid nuclei compounds of this invention are those wherein n is 0; each of R and R$^1$ is hydrogen, R$^2$ is hydrogen; and Y is selected from the group consisting of —CN, —COOH, and —COO-alkyl having from 1 to 4 carbon atoms in the alkyl.

A preferred group of 3-(substituted)vinyl-7-acylamido cephalosporin acid and salt antibiotic compounds of this invention are those of formula (V) above wherein n is 0; R is selected from the group consisting of chloroacetyl, bromoacetyl, 2-thienylacetyl, cyanoacetyl, sydnoneacetyl, a radical of the formula

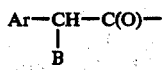

wherein Ar is 2-thienyl, or phenyl, and B is —OH, —COOH, —CN, —N$_3$, —C(O)NH$_2$,

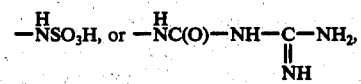

or R is the group

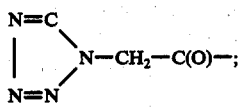

R$^1$ is hydrogen;
R$^2$ is hydrogen;
Y is selected from the group consisting of —CN, —COOH, and —COO-alkyl having from 1 to 4 carbon atoms in the alkyl, and the pharmaceutically acceptable salts of such compounds.

A few examples of the various compounds represented by the above formula are given. A 3-(substituted) vinyl cephalosporin sulfoxide ester is represented by:
Benzhydryl 3-(2'-cyanovinyl)-7-(2'-thienylacetamido)-3-cepham-4-carboxylate-1-oxide
which can be obtained from cephalothin after 3-hydroxymethyl group formation, esterification, sulfoxide formation, 3-formyl group formation, and reaction thereof with a phosphorane such as cyanomethylene triphenylphosphorane.

An example of a 3-(substituted) vinyl cephalosporin sulfide ester of the above formula is
tert-Butyl 3-(2'-carbamylvinyl)-7-[D-α-(tert-butoxycarbonylamino)-α-phenylacetamido]-3-cephem-4-carboxylate, prepared by reducing the corresponding sulfoxide.

An example of a nucleus compound of the above defined type is a p-toluenesulfonic acid salt of tert-butyl 3-(2'-tert-butyloxycarbonylvinyl)-3-cephem-4-carboxylate, prepared by cleaving the 7-acyl side chain.

An example of a free 3-(substituted)vinyl cephalosporin nucleus acid compound of the above type is 3-(2'-ethoxycarbonylvinyl)-7-amino-3-cephem-4-carboxylic acid, which can be recovered as the zwitterion.

An example of a 3-(substituted)vinyl cephalosporin acid antibiotic compound of the invention is 3-(2'-carboxyvinyl)-7-phenoxyacetamide-3-cephem-4-carboxylic acid.

Other examples of the various compounds of the invention will be illustrated below.

The 3-(substituted)vinyl cephalosporin compounds of this invention can be prepared by reacting a 3-formyl cephalosporin sulfide or sulfoxide ester with a phosphorane of the formula

$$R_1R_2R_3P=CH-Y$$

wherein each of $R_1$, $R_2$, and $R_3$ is bonded to the phosphorus atom and is a hydrocarbon radical free of aliphatic unsaturation containing from 1 to 8 carbon atoms, preferably phenyl or n-butyl; Y is a group as defined above, to convert the 3-formyl group of the cephalosporin sulfide or sulfoxide ester starting material to a 3-(substituted)vinyl cephalosporin sulfoxide ester. Thereafter, a variety of conventional process routes exemplified below to obtain any desired cephalosporin antibiotic compounds can be used. The 3-(substituted)-vinyl cephalosporin sulfoxide ester intermediates, obtained in the above described "Wittig" reaction [see Organic Reactions, Vol. 14, (1965) Chapter 3, pp 270–490] can be reduced to the sulfide stage, the 7-acyl side chain can be cleaved to obtain the 7-amino compound and converted to a salt if desired, the 7-amino compound can be re-acylated with any desired acyl group, and then any protecting groups can be removed, all by methods now known, to obtain the desired 3-(substituted)vinyl cephalosporanic acid derivative which can be isolated from the reaction mixture, purified, and converted to pharmaceutical dosage form for use as an antibiotic in therapy against a variety of infectious diseases.

Alternatively, the 3-(substituted)vinyl cephalosporin sulfoxide ester, obtained from the first step of the process described above, can be reduced, the 7-acyl group can be cleaved and to obtain the new 3-(substituted)vinyl-7-amino-3-cephem-4-carboxylic acid ester compounds, or in addition the ester group can be removed to obtain the 7-amino-acid (both esters and acids being referred to as nucleus compounds), which are useful as intermediates in preparing cephalosporin antibiotics by acylating the 7-amino group by conventional acylation procedures to obtain the desired 3-(substituted)vinyl cephalosporanic acid antibiotic compound.

The process can be applied to any 3-formyl cephalosporin sulfide or sulfoxide ester. Starting materials can be obtained from a variety of sources. For example, penicillin V and penicillin G and numerous other penicillins can be converted by procedures now known to the corresponding desacetoxycephalosporin esters having the phenoxyacetyl (from penicillin V) or the phenylacetyl (from penicillin G) by the Morin/Jackson process described in U.S. Pat. No. 3,275,626, as improved by the Cooper (U.S. application Ser. No. 838,697, filed July 2, 1969 now U.S. Pat. No. 3,647,787) and Hatfield (U.S. application Ser. No. 799,504, filed February 14, 1969 now U.S. Pat. No. 3,591,585) inventions. Such desacetoxycephalosporin esters can be converted to the 3-hydroxymethyl cephalosporin esters, and oxidized to the corresponding 3-formyl-cephalosporin sulfoxide esters, as set forth in my application Ser. No. 58,678, filed July 27, 1970 now U.S. Pat. No. 3,674,784, which is incorporated herein by reference thereto. In addition, the 3-formyl cephalosporin sulfide or sulfoxide ester can be obtained from cephalosporin C and its derivatives. For example, 7-aminocephalosporanic acid can be treated with an esterase from Bacillus subtilis or with orange peel esterase to form 7-aminodesacetylcephalosporanic acid which can be acylated on the 7-amino group and then esterified, e.g., with diphenyldiazomethane by known procedures to form a sulfide starting material for use in making compounds of this invention. Alternatively, the compound can be oxidized to the sulfoxide to form, e.g., benzhydryl 7-(protected amino)desacetylcephaloporanate ester sulfoxide, for use in the process of making compounds of this invention. Normally, when starting from cephalosporin C it will be preferred to protect the 5-amino group in the 5-aminoadipoyl side chain of cephalosporin C by procedures now known, for example, by benzyloxycarbonyl or tert-butoxycarbonyl; or by an $C_2$ to $C_6$-alkanoyl group and to protect the carboxyl groups with an easily removed ester. Then the protected cephalosporin C derivative can be oxidized with a peracid such as metachloroperbenzoic acid, or hydrogen peroxide, and the 3-acetoxymethyl group can be converted to the 3-hydroxymethyl group by known chemical or enzymatic procedures, e.g., by treatment with orange peel esterase to obtain the protected 3-hydroxymethylcephalosporin C sulfoxide ester derivative. This derivative can be oxidized with chromium trioxide, manganese dioxide, dichlorodicyanoquinoline, nickel peroxide or the like to obtain the 3-formyl cephalosporin C sulfoxide ester starting material. The use of chromium trioxide, particularly chromium trioxide in sulfuric acid/water, commonly referred to as "Jones Reagent" [Fieser and Fieser, Reagents for Organic Synthesis, Vol. 1, page 142, John Wiley and Sons, Inc. 1967] is preferred. Since it is contemplated that the 5-aminoadipoyl side chain will be cleaved by known procedures later on in the process it is not essential to protect the reactive groups therein, but better yields of the nucleus 7-amino cephalosporin compounds are generally obtained if those groups are protected.

The phosphorane compounds which are used in preparing the compounds of this invention can be prepared by conditions which are well known. Some of such phosphorane compounds are commercially available. Procedures for making various phosphoranes are disclosed, e.g., in Journal of Organic Chemistry, Vol. 22, (1957), pp. 41 to 45 in an article entitled "Phosphinemethylenes. II. Triphenylphosphineacylmethylenes" by F. Ramirez and S. Dershowitz; Journal of the Chemical Society, 1959, pp. 3874–3876, in an article entitled "The Phosphobetaines: Preparation and Properties" by S. Trippett and D. M. Walker; Journal of Organic Chemistry, Vol. 27, 1962, pp. 998–1000 in article entitled "The Preparation and Reactions of Some Halophosphoranes" by D. B. Denney and S. T. Ross; and in Organic Reactions, Vol. 14, (1965), Chapter 3, pp. 270–490. Published by John Wiley and Sons, New York, London, and Sydney.

The phosphorane which is used in preparing the new substituted vinyl cephalosporin compounds of this invention could be one which is unstabilized. However, I prefer that the phosphorane be one which is partially stabilized, for instance, with an electron withdrawing group. However, the phosphorane should not be so stabilized that it will not react with the 3-formyl cephalosporin sulfoxide ester. Examples of preferred phosphoranes include those of the formula

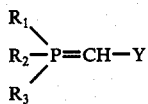

where each of $R_1$, $R_2$, and $R_3$ is phenyl or $C_1$ to $C_6$-alkyl such as methyl, ethyl, propyl, n-butyl, and is preferably phenyl or n-butyl and Y is —C(O)OR³, where R³ is $C_1$ to $C_4$-alkyl, methoxybenzyl, nitrobenzyl, benzhydryl, or 2,2,2-trichloroethyl or Y is —CN,
—CHO,
—X-$C_1$ to $C_4$-alkyl or —X-phenyl where X is oxygen or sulfur
—C(O)-$C_1$ to $C_3$-alkyl, —C(O)phenyl, or benzylcarbonyl
—C(O)NH₂,
—NO₂,
—S(O)-$C_1$ to $C_4$-alkyl,
—S(O)₂-$C_1$ to $C_4$-alkyl,
—Cl or —Br,
—CF₃
—$C_1$ to $C_6$-alkyl
—phenyl
—phenyl substituted with chlorine, bromine, iodine, —NO₂, —CN, —CF₃, $C_1$ to $C_4$-alkyl, $C_1$ to $C_4$-alkyl-X—, or —C(X)-X-$C_1$ to $C_4$-alkyl where X in each case is oxygen or sulfur or Y is

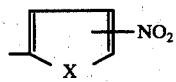

where X is oxygen or sulfur, exemplified by (Propyloxycarbonylmethylene)triphenylphosphorane,
(p-Methoxybenzyloxycarbonylmethylene)triphenylphosphorane,
(p-Nitrobenzyloxycarbonylmethylene)triphenylphosphorane,
(Cyanomethylene)triphenylphosphorane,
(Benzhydryloxycarbonylmethylene)triphenylphosphorane,
(2,2,2-Trichloroethoxycarbonylmethylene)triphenylphosphorane
(Formylmethylene)triphenylphosphorane,
(Acetylmethylene)triphenylphosphorane
(Chloromethylene)triphenylphosphorane,
(Bromomethylene)triphenylphosphorane,
(Chloromethylene)triphenylphosphorane,
(Ethoxymethylene)triphenylphosphorane,
(Phenoxymethylene)triphenylphosphorane,
(n-Butylthiomethylene)triphenylphosphorane,
(Phenylthiomethylene)triphenylphosphorane,
(Ethylcarbonylmethylene)triphenylphosphorane
(Phenylcarbonylmethylene)triphenylphosphorane
(carbamylmethylene)triphenylphosphorane,
(Benzylcarbonylmethylene)triphenylphosphorane
(Nitromethylene)triphenylphosphorane,
(Methylsulfinylmethylene)triphenylphoshorane
(n-Propylsulfonylmethylene)triphenylphosphorane,
(Trifluoromethylmethylene)triphenylphosphorane,
(Hexylmethylene)triphenylphosphorane,
(Phenylmethylene)triphenylphosphorane
(4-Chlorophenylmethylene)triphenylphosphorane,
(3,4-Dibromophenylmethylene)triphenylphosphorane,
(3-Iodophenylmethylene)triphenylphosphorane,
(4-Nitrophenylmethylene)triphenylphosphorane,
(4-Nitro-2-thienylmethylene)triphenylphosphorane,
(5-Nitro-2-furylmethylene)triphenylphosphorane,
(5-Nitro-2-thienylmethylene)triphenylphosphorane
(4-Cyanophenylmethylene)triphenylphosphorane,
(4-Trifluoromethylphenylmethylene)triphenylphosphorane,
(4-Methylphenylmethylene)triphenylphosphorane,
(4-Methoxyphenylmethylene)triphenylphosphorane
(4-Methoxycarbonylphenylmethylene)triphenylphosphorane, and the like.

The corresponding tri-n-butylphosphoranes are also preferred examples.

Specific cephalosporin starting materials, intermediates, and products of this invention are named, for convenience, by use of the "cepham" nomenclature system which has been adapted to cephalosporin compounds from an analogous nomenclature system based on "penam" for naming specific penicillin compounds. "Penam" nomenclature for the penicillins is described by Sheehan, Henery-Logan, and Johnson in the Journal of the American Chemical Society (JACS), 75, 3292, footnote 2 (1953). This system was adapted to the cephalosporins by Morin et al in JACS, 84 3400 (1962). In accordance with these systems of nomenclature, "penam" and "cepham" refer respectively to the following saturated ring systems

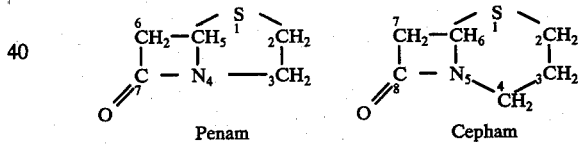

Penam          Cepham

"Cephem" refers to the cepham ring structure containing a double bond, the position of which is indicated by an integer preceeding the "cephem" denoting the lowest numbered carbon atom to which the double bond is connected. Some persons choose to indicate the position of the double bond by use of a prefix "Δ" with an integer superscript, or the word "delta" with the same number relationship. However, we prefer not to use the delta symbol. For example, a 3-formyl cephalosporin sulfoxide ester used as a starting material in preparing the compounds of this invention can be named tert-butyl 3-formyl-7-phenoxyacetamido-3-cephem-4-carboxylate-1-oxide. A compound of this invention can be named 3-(2'-carboxyvinyl)-7-[D-α-amino-α-phenylacetamido]-3-cephem-4-carboxylic acid.

In preparing the compounds, the phosphorane (Wittig reagent) is commingled with the 3-formyl cephalosporin sulfide or sulfoxide ester, preferably while the latter is dissolved, at least partially, in a substantially anhydrous organic liquid medium at temperatures above the freezing point of the mixture to reflux temperatures, (generally not above 150° C) until the 3-(substituted)-vinyl cephalosporin sulfide or sulfoxide ester is formed. The mixture may be allowed to stand for several days, but the mixture is preferably agitated to insure contact of the reactants and shorten reaction time. When the reaction is completed the 3-(substituted)-vinyl cephalosporin sulfide or sulfoxide ester can be separated from the phosphine oxide by-product, and recovered from the reaction mixture, and purified by conventional means. A molar equivalent of the phosphorane reactant, relative to the molar content of the 3-formyl cephalosporin sulfide or sulfoxide ester starting material, is usually sufficient although efficient practice may dictate that an excess of the phosphorane reagent be used to insure complete reaction of the more expensive 3-formyl cephalosporin.

Examples of 3-(substituted)vinyl cephalosporin sulfide or sulfoxide esters of this invention and the Wittig reagents which are reacted with the 3-formyl cephalosporin sulfoxide ester to prepare them include:

tert-Butyl 3-(2'-isopropyloxycarbonylvinyl)-7-(5'-acetylaminoadipolylamido)-3-cephem-4-carboxylate-1-oxide from (isopropyloxycarbonyl methylene)triphenylphosphorane;

tert-Pentenyl 3-(2'-cyanovinyl)-7-phenoxyacetamido-3-cephem-4-carboxylate-1-oxide from (cyanomethylene)triphenylphosphorane;

tertPentynyl 3-(2'-formylvinyl)-7-(2',2'-dimethyl-2'-phenylacetamido)-3-cephem-4-carboxylate-1-oxide from (formylmethylene)-triphenylphosphorane;

tert-Butyl 3-(2'-ethoxycarbonylvinyl)-7-phenylacetamido-3-cephem-4-carboxylate-1-oxide from (ethoxycarbonylmethylene)triphenylphosphorane;

Benzhydryl 3-cyanovinyl-7-acetamido-3-cephem-4-carboxylate-1-oxide from (cyanomethylene)triphenylphosphorane;

p-Nitrobenzyl 3-(2'-methoxyvinyl)-7-phenylacetamido-3-cephem-4-carboxylate-1-oxide from (methoxymethylene)triphenylphosphorane;

2,2,2-Trichloroethyl 3-(2'-ethylthiovinyl)-7-phenoxyacetamido-3-cephem-4-carboxylate-1-oxide from (ethylthiomethylene)triphenylphosphorane;

Benzhydryl 3-(2'-acetylvinyl)-7-thienylacetamido-3-cephem-4-carboxylate-1-oxide from (acetylmethylene)triphenylphosphorane;

Phenacyl 3-(2'-carbamylvinyl)-7-(5'-(protected amino)-adipoylamido)-3-cephem-4-carboxylate-1-oxide from (carbamylmethylene)-triphenylphosphorane;

Trimethylsilyl 3-[2'-(4''-nitrobenzoyl)vinyl]-7-phenoxyacetamido-3-cephem-4-carboxylate-1-oxide from (4-nitrobenzoylmethylene)triphenylphosphorane;

Succinimidomethyl 3-(2'-methylsulfinylvinyl)-7-(4'-hydroxyphenoxyacetamido)-3-cephem-4-carboxylate-1-oxide from (methylsulfinylmethylene)triphenylphosphorane;

Phthalimidomethyl 3-(2'-propylsulfonylvinyl)-7-(3'-hydroxyphenylacetamido)-3-cephem-4-carboxylate-1-oxide from (propylsulfonylmethylene)triphenylphosphorane;

2-Iodoethyl 3-(2'-trifluoromethylvinyl)-7-phenylmercaptoacetamido-3-cephem-4-carboxylate-1-oxide from trifluoromethylmethylene)-triphenylphosphorane.

p-Methoxybenzyl 3-[2'-nitrobenzyl)vinyl]-7-phenoxyacetamido-3-cephem-4-carboxylate-1-oxide from 4-nitrobenzylidenetriphenylphosphorane;

Benzyl 3-[2'-(4''-methoxyphenyl)vinyl]-7-[D-α-phenyl-α-(tert-butoxycarbonylamino)acetamido]-3-cephem-4-carboxylate-1-oxide from (4-methoxyphenylmethylene)triphenylphosphorane;

t-Butyl 7-acetamido-3-(2'-ethoxycarbonylvinyl)-3-cephem-4-carboxylate from (ethoxycarbonylmethylene)-triphenylphosphorane;

Benzhydryl 7-acetamido-3-[2'-(5''-nitrothienyl)vinyl]-3-cephem-4-carboxylate from (5-nitro-2-thienylmethylene)triphenylphosphorane;

Benzhydryl 7-formamido-3-[2'-(5''-nitrofuryl)vinyl]-3-cephem-4-carboxylate from (5-nitro-2-furylmethylene)triphenylphosphorane, and the like.

Examples of vinyl cephalosporin esters of this invention are those of the above 3-(substituted)vinyl cephalosporin sulfoxide esters, listed above, which have been reduced by known methods to reduce the sulfur in the 1-position to the bivalent sulfide state. Procedures for reducing $\Delta^3$-cephalosporin sulfoxide acids and esters to the corresponding sulfide state are described, for example, in U.S. application Ser. No. 764,925, filed Oct. 3, 1968. Briefly, by that process a 3-(substituted)vinyl cephalosporin sulfoxide ester of this invention can be treated with a reducing agent selected from the group consisting of:

1. hydrogen in the presence of a hydrogenation catalyst;
2. stannous, ferrous, cuprous, or manganous cations,
3. dithionite, iodide, or ferrocyanide anions,
4. trivalent phosphorus compounds having a molecular weight below about 500,
5. halosilane compounds of the formula

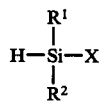

where X is chlorine, bromine, or iodine, and each of $R^1$ and $R^2$ is hydrogen, chlorine, bromine, iodine, or a hydrocarbon radical free from aliphatic unsaturation and having from 1 to 8 carbon atoms, and 6. a chloromethylene iminium chloride of the formula

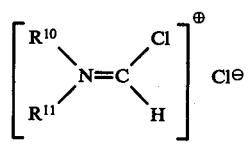

wherein each of $R^{10}$ and $R^{11}$ taken separately denote a $C_1$ to $C_3$-alkyl or taken together with the nitrogen to which they are bonded complete a monocyclic heterocyclic ring having from 5 to 6 ring forming atoms and a total of from 4 to 8 carbon atoms, in the presence or absence of an activating agent (depending upon the choice or reducing agent) which is an acid halide of an acid of carbon, sulfur or phosphorus, which acid halide is inert to reduction by the reducing agent, and which acid halide has a second order hydrolysis constant equal to or greater than that of benzoyl chloride, in a substantially anhydrous liquid medium at a temperature of from about −20° C to about 100° C to form the 3-(substituted)vinyl cephalosporin ester.

When the sulfoxide reduction is completed the 3-(substituted)vinyl cephalosporin ester can be treated by alternative methods. If the 7-acylamido side chain is the desired one, then the ester group can be removed by known methods to obtain the antibiotically active 3-(substituted)vinyl cephalosporin acid, either as such, or as a pharmaceutically acceptable salt. An example of such an acid is 3-(2′-ethoxycarbonylvinyl)-7-phenoxyacetamido-3-cephem-4-carboxylic acid, which can be derived from penicillin V. Another example is 3-(2′-carboxyvinyl)-7-(2″-thienylacetamido)-3-cephem-4-carboxylic acid, sodium salt, which can be derived from a cephalothin starting material. However, in some cases, it is desired to remove the 7-acyl group, such as phenoxyacetyl (derived from penicillin V) or phenylacetyl (derived from penicillin G) to obtain the respective 7-amino 3-(substituted)vinyl cephalosporin ester or acid nucleus compound, either as such or as an acid addition salt thereof, for use in making 3-(substituted)vinyl cephalosporin antibiotic acid and salt compounds, some of which have an antibiotic spectrum which is different from the presently commercially available antibiotics. In such cases, the 7-acylamido-3-(substituted)-vinyl cephalosporin ester is treated by any of a variety of known procedures such as the PCl₅/pyridine: methanol: water procedure to cleave the 7-acyl side chain. Alternatively, a nitrosyl chloride cleavage procedure described in U.S. Pat. No. 3,188,311, or an improved procedure described in U.S. Pat. No. 3,261,832 can be used. Other 7-acyl cleavage procedures for cephalosporin compounds are described, e.g., in U.S. Pat. No. 3,272,809, and in U.S. application Ser. No. 805,823, filed Mar. 10, 1969. The 7-amino 3-(substituted)vinyl cephalosporin ester compounds can be purified and recovered by procedures, now known, such as that described in U.S. Pat. No. 3,507,860. A few examples of 7-amino 3-(substituted)vinyl cephalosporin ester compounds of this invention include tert-Butyl 7-amino-3-(2′-methoxycarbonylvinyl)-3-cephem-4-carboxylate p-toluenesulfonate,
p-Nitrobenzyl 7-amino-3-(2′-carboxyvinyl)-3-cephem-4-carboxylate-4-chlorobenzenesulfonate salt,
Benzhydryl 7-amino-3-[2′-(4″-nitrobenzyl)vinyl]-3-cephem-4-carboxylate 1-naphthylenesulfonate salt,
7-Amino-3-(2′-cyanovinyl)-3-cephem-4-carboxylic acid,
7-Amino-3-(2′-tert-butyloxycarbonylvinyl)-3-cephem-4-carboxylic acid 3,4-dichlorobenzenesulfonate salt, and the like.

The 7-amino 3-(substituted)vinyl cephalosporin ester and acids, and salts thereof are then re-acylated in single or multiple step processes to prepare new 3-(substituted)vinyl cephalosporin antibiotics of this invention. For example, these 7-amino 3-(substituted)vinyl cephalosporin compounds can be acylated with D-phenyl-glycine, D-(3-hydroxyphenyl)glycine, D-(4-hydroxyphenyl)glycine, D-(3,4-dichlorophenyl)glycine or similar compounds, in which the amino groups are protected using the known mixed anhydride, carbodiimide, acyl halide, or other activated intermediates to obtain the respective 7-[2′-D-N-protected-amino-2′-phenylacetamido]-3-(substituted)vinyl cephalosporin acid or ester. The amino and any carboxyl protecting groups can be removed by known procedures to obtain the respective 3-(substituted)vinyl cephalosporanic acid. Examples include:

3-(2′-carboxyvinyl)-7-[D-2′-amino-2′-phenylacetamido]-3-cephem-4-carboxylic acid,
3-(2′-ethoxycarbonylvinyl)-7-[D-2′-amino-2′-(3-hydroxyphenyl)-acetamido]-3-cephem-4-carboxylic acid,
3-(2′-cyanovinyl)-7-[D-2′-amino-2′-(4-hydroxyphenyl)acetamido]-3-cephem-4-carboxylic acid,
3-[2′-(4″-nitrobenzyl)vinyl]-7-[D-2′-amino-2′-(3″,5″-dichloro-4″-hydroxyphenyl)acetamido]-3-cephem-4-carboxylic acid, and the like, which can be recovered as the zwitterions, acid addition salt, or salts with pharmaceutically acceptable cations.

The 7-amino-3-(substituted)vinyl cephalosporin compounds can also be acylated with phenylmalonic acid or mandelic acid derivatives to obtain compounds such as 3-(2′-carboxyvinyl)-7-[D-2′-carboxy-2′-phenylacetamido]-3-cephem-4-carboxylic acid,
3-(2′-ethoxycarbonylvinyl)-7-[D-2′-carboxy-2′-(3″-hydroxyphenyl)acetamido]-3-cephem-4-carboxylic acid,
3-[2′-(4″-nitrobenzyl)vinyl]-7-[D-2′-carboxy-2′-(4″-hydroxyphenyl)acetamido]-3-cephem-4-carboxylic acid,
3-(2′-carboxyvinyl)-7-[D-2′-hydroxy-2′-phenylacetamdo]-3-cephem-4-carboxylic acid, and the like.

The 7-amino 3-(substituted)vinyl cephalosporin compounds can be acylated with nitrogen containing heterocyclic acyl groups of the formula

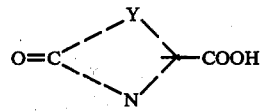

described, e.g. in U.S. Pat. No. 3,308,128. A few examples of 3-substituted)vinyl cephalosporins of this invention including such groups as:

3-(2′-carboxyvinyl)-7-(5-oxopyrrolidine-2-carbonamido)-3-cephem-4-carboxylic acid,
3-[2′-(4″-nitrobenzyl)vinyl]-7-(1′-propyl-5-oxopyrrolidine-3-carbonamido)-3-cephem-4-carboxylic acid,
3-(2′-formylvinyl)-7-(1-methyl-6-oxonicotinamido)-3-cephem-4-carboxylic acid, and the like.

Similarly, the 7-amino 3-(substituted)vinyl cephalosporin ester or acid compounds of this invention may be acylated with the heterocyclic acyl groups disclosed in Flynn U.S. Pat. No. 3,218,318, heterocyclic acyl groups disclosed in Flynn U.S. Pat. No. 3,218,318; Takano et al., U.S. Pat. Nos. 3,516,997, 3,360,515, and 3,365,449 to obtain new 3-(substituted)vinyl cephalosporin compounds which are useful as intermediates, or when converted to the acid form, as cephalosporin antibiotics.

The 7-amino-3-(substituted)vinyl-3-cephem-4-carboxylic acid and ester compounds and salts thereof can be acylated on the 7-amino nitrogen with a large variety of acyl groups known to contribute at least some antibiotic activity to the resulting cephalosporin acids obtained therefrom. Numerous prior patent references could be cited. A few examples are given here:

The substituted propionic acids in U.S. Pat. No. 3,338,896;

The α-substituted carboxylic acids in U.S. Pat. No. 3,338,897;

The α- or β-azido carboxylic acids in U.S. Pat. No. 3,340,257;

The N-containing heterocyclic carboxylic acids disclosed in U.S. Pat. No. 3,360,515;

The substituted thiocarboxylic acids in U.S. Pat. No. 3,365,449;

The substituted phenylacetyl chlorides in U.S. Pat. No. 3,431,259;

The α, β-unsaturated carboxylic acids in U.S. Pat. No. 3,453,272;

The α-(pyridylthio)acetyl chloride in U.S. Pat. No. 3,503,967;

The 5-methyl-1H-tetrazole-1-acetic acid and other heterocyclic acids in U.S. Pat. No. 3,516,997;

The sydnone acids, e.g. sydnone-3-acetic acid sydnone-3-propionic acid, and other such acids in U.S. Pat. No. 3,530,123.

However, a preferred group of 7-acyl side chains for the compounds of this invention are those having the general formula

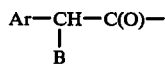

where Ar is 2- or 3-thienyl, 2- or 3-furyl, phenyl, phenyl substituted with chlorine or bromine at the 3-, 4-, and-/or the 5-position, sydnoneacetyl, tetrazoleacetyl, and B is —NHSO$_3$H, —NH$_2$,

—COOH, —OH, —CN, —N$_3$, or —C(O)NH$_2$. The 3-(substituted)vinyl cephalosporanic acid derivatives containing some of these side chains provide compounds with different antibiotic spectra than earlier known cephalosporin antibiotics.

The 3-(substituted)vinyl cephalosporanic acid, or pharmaceutically acceptable salts thereof, such as the sodium, potassium, calcium, cyclohexanebis(methylamine), ammonium, monoethanolamine, and the like, can be formulated into liquid pharmaceutical form, e.g., in water, isotonic saline, or the like and administered by intramuscular injections or by intravenous administration procedures to provide dosages of from about 125 mg. to 16 grams a day depending upon the patient's body weight, the disease condition being treated, and other factors of concern to the patient's physician. In some cases, these compounds could be administered 1 to 6 times per day by the oral route, in dry encapsulated or tableted formulations containing from 125 to 500 mg. per tablet or capsule in which case the compound would be diluted with pharmaceutical grade starch, talc, carboxymethylcellulose or other conventional diluent.

As indicated above, the 3-(substituted)vinyl cephalosporin compounds of this invention are generally useful as antibiotics or as intermediates in processes for preparing such antibiotically active compounds. The 7-acylamido-3-(substituted)vinyl cephalosporanic acids, salts, and zwitterions have antibiotic activity against a variety of Gram positive or Gram negative microorganisms. Those acid compounds in which the substituent on the vinyl grouping is an election withdrawing group have been found to have much better antibiotic activity against Gram negative microorganisms than against Gram positive microorganisms. Some of these compounds have, surprisingly, shown antibiotic activity against *Serratia marcescens, Psuedomonas aeruginosa,* as well as against indole-positive Proteus strains, and some Enterobacter species of microorganisms in standard primary screening tests.

The invention is further illustrated by the following detailed examples which are not intended to limit the scope of the invention.

EXAMPLE 1 tert-butyl 3-(2'-ethoxycarbonylvinyl)-7-phenoxyacetamido-3-cephem-4-carboxylate-1-oxide

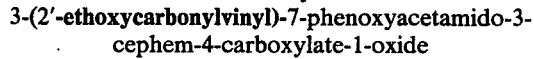

To a solution of 0.5 millimole of tert-butyl 3-formyl-7-phenoxyacetamido-3-cephem-4-carboxylate-1-oxide in 10 cc. of dry benzene was added 175 mg. (1 equivalent) of (carbethoxymethylene)-triphenylphosphorane. After allowing the reaction mixture to stand at room temperature for 11 days, the solvent was removed under reduced pressure, the residue taken up in hot ethyl acetate, and cooled to yield 140 mg. of crystalline triphenylphosphine oxide (m.p., 155°-157° C.) as by-product.

The mother liquors were purified by preparative thin-layer chromatography on silica gel, eluting with a 1:1 v/v benzene-ethyl acetate mixture to give 247 mg. of the above-named product as a non-crystalline material. The infrared (IR) and nuclear magnetic resonance (NMR) spectra were in accord with the structure for the named product.

EXAMPLE 2 tert-butyl 3-(2'-ethoxycarbonylvinyl)-7-phenoxyacetamido-3-cephem-4-carboxylate

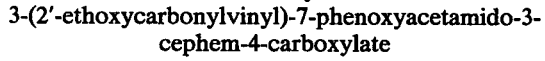

To a cooled (0° C. to 5° C.) solution of 200 mg. of tert-butyl 3-(2'-ethoxycarbonylvinyl)-7-phenoxyacetamido-3-cephem-4-carboxylate-1-oxide in 10 cc. of dry 8:2 v/v acetonitrile-dimethylformamide mixture there was added 400 mg. of anhydrous stannous chloride and then 0.45 cc. of acetyl chloride. After 15 minutes at 0° C. to 5° C. and 2 hours at room temperature the solvent was removed under reduced pressure, the residue taken up in ethyl acetate, and washed with saturated aqueous sodium chloride solution, with cold 5 percent hydrochloric acid, saturated aqueous sodium bicarbonate solution, saturated aqueous sodium chloride solution, and then dried over magnesium sulfate. The mixture was then filtered and the filtrate was evaporated under reduced pressure to give 175 mg. of a yellow oil which was purified by preparative thin-layer chromatography on silica gel, with elution by a 3:1 v/v benzene:ethyl acetate mixture. The above-named ester product would not crystallize, but was characterized by its NMR spectrum (vinyl protons at 6.01δ and 7.96δ (J = 16 Hz).

EXAMPLE 3

3-(2'-ethoxycarbonylvinyl)-7-phenoxyacetamido-3-cephem-4-carboxylic acid

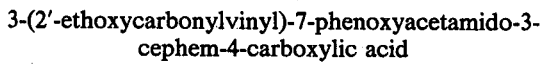

A solution of 75 mg. of tert-butyl 3-(2'-ethoxycarbonylvinyl)-7-phenoxyacetamido-3-cephem-4-carboxylate in 10 cc. of 98–100 percent formic acid, any remainder being water, was allowed to stand at room temperature for 1.5 hours. After evaporation under reduced pressure of the formic acid, isolation of the acidic material by extraction provided 55 mg. of the desired above-named acid, which could be crystallized from ether or ethanol, m.p., 193°–196° C. The IR, NMR, and ultraviolet (UV) spectra and elemental analyses were in accord with the assigned structure.

Analysis, Calc.: C, 55.55; H, 4.66; N, 6.48.
Found: C, 55.37; H, 4.89; N, 6.43.

This compound showed activity as an antibiotic in gradient plate tests against a variety of both Gram positive and Gram negative microorganisms.

EXAMPLE 4 tert-butyl 7-amino-3-(2'-ethoxycarbonylvinyl)-3-cephem-4-carboxylate-p-toluene sulfonate To a solution of 1.75 millimoles of oily tert-butyl 3-(2'-ethoxycarbonylvinyl)-7-phenoxyacetamido-3-cephem-4-carboxylate in 50 cc. of dry benzene was added 1.4 equivalents (196 milligrams) of dry pyridine and 1.4 equivalents (511 mg.) of phosphorus pentachloride. This mixture was heated at 58°–60° C. under a nitrogen atmosphere for 2 hours, evaporated under reduced pressure to dryness and 50 cc. of cold (0° C. to 5° C.) methanol was added. After two hours at room temperature, the methanol was removed under reduced pressure and the residue was dissolved in 50 cc. of cold (0° C. to 5° C) 1/1 v/v tetrahydrofuran: pH 4.5 aqueous buffer. After 30 minutes at room temperature, the volume of the mixture was concentrated under reduced pressure, ethyl acetate was added, and the pH was adjusted to 6.5 with solid sodium bicarbonate. The organic layer was separated and washed twice with saturated aqueous sodium chloride solution, dried over magnesium sulfate, filtered and evaporated under reduced pressure to about 15 ml. A solution of 330 mg. of p-toluenesulfonic acid monohydrate (1 equivalent) in ethyl acetate was added. Refrigeration of the mixture produced 571 mg. of crystalline product. Recrystallization from isopropanol provided the titled ester-salt product, m.p., 151°–155° C., whose IR, UV, NMR, and elemental analyses were in accord with the structure for the desired structure.

Analysis, Calc: C, 52.45; H, 5.74; N, 5.32.
Found: C, 52.50; H, 5.62; N, 5.32.

EXAMPLE 5 tert-BUTYL 7-AMINO-3-(2'-tert-butoxycarbonylvinyl)-3-cephem-4-carboxylate-p-toluenesulfonate To a stirred solution of tert-butyl 3-formyl-7-phenoxyacetamide-3-cephem-4-carboxylate-1-oxide (3.7 g., 8.55 mmoles), prepared as described above, in a mixture of 100 cc. of dry benzene and 100 cc. of isopropanol there was added 2.88 g. (0.95 equivalent, 8.12 mmoles) of (tert-butoxycarbonylmethylene)-triphenylphosphorane. After sixty-eight hours at room temperature, the solvent was removed under reduced pressure to leave as residue crude tert-butyl 3-(2'-tert-butoxycarbonylvinyl)-7-phenoxyacetamido-3-cephem-4-carboxylate-1-oxide.

This residue was dissolved in a mixture of 40 cc. of dry dimethylformamide and 40 cc. of dry acetonitrile, cooled to 0° C. to 5° C., and then 2.84 g. (17.1 mmoles) of potassium iodide and 8.6 cc. of acetyl chloride were added. After 30 minutes at 0°–5° C. and thirty minutes at room temperature, the reaction mixture was concentrated under reduced pressure, the residue was taken up in benzene, the benzene mixture was washed twice with saturated aqueous sodium chloride solution, twice with cold 5 percent hydrochloric acid solution, twice with saturated aqueous sodium bicarbonate solution, once with 10% w/v aqueous sodium thiosulfate, twice with saturated aqueous sodium chloride solution, dried over magnesium sulfate plus charcoal, filtered, and evaporated under reduced pressure to give as residue 6.5 g. of crude tert-Butyl 3-(2'-tert-butoxycarbonylvinyl)-7-phenoxyacetamido-3-cephem-4-carboxylate. This reduced product was combined with product from a similar reaction and purified by column chromatography over silica gel—15 percent water mixture. A portion of the purified ester, 500 mg., was dissolved in 70 ml. of benzene and the volume reduced to 50 cc. by distillation. Then 110 mg. (1.4 equivalents) of dry pyridine and 282 mg. (1.4 equivalents) of phosphorus pentachloride were added, and the reaction mixture, under $N_2$ atmosphere, was heated at 50°–55° C. for about 1.5 hours to form the imino-chloride. After cooling to room temperature, the benzene was removed under reduced pressure and the residue was taken up in 0° C. to 5° C. methanol. After three hours at room temperature to insure formation of the methyl ether, the excess methanol was removed under reduced pressure and the residue was dissolved, with cooling (0° to 5° C.) in 30 cc. of tetrahydrofuran (THF) and 30 cc. of pH 4.5 aqueous buffer solution. After one-half hour, the THF was removed under reduced pressure, ethyl acetate was added and the pH was adjusted to 6.5 with solid sodium bicarbonate. The organic layer was separated, washed with saturated aqueous sodium chloride solution, dried over magnesium sulfate, filtered, and evaporated under reduced pressure to dryness. The tert-butyl 3-(2'-tert-butoxycarbonylvinyl)-7-amino-3-cephem-4-carboxylate residue was taken up in methylene chloride and 172 mg. (0.9 mmoles) of p-toluenesulfonic acid was added in a methylene chloride:ethyl acetate mixture. The title compound crystallized upon standing, m.p., 166°–168° C., and was characterized by IR, UV, NMR spectral analyses and elemental analysis.

Analysis, Calc.: C, 54.13; H, 6.18; N, 5.05.
Found: C, 53.92; H, 6.16; N, 5.18.

EXAMPLE 6 tert-butyl 3-(2'-tert-butoxycarbonylvinyl)-7-(2'-tert-butoxycarbonyl-2'-phenylacetamido)-3-cephem-4-carboxylate To a cooled (0°–5° C.) suspension of 277 mg. (0.5 mmole) of tert-butyl 7-amino-3-(2'-tert-butoxycarbonylvinyl)-3-cephem-4-carboxylate-p-toluenesulfonate and 420 mg. (5 equivalents) of sodium bicarbonate in 20 cc. of dry acetone there was added about 1 mmole of tert-butyl phenylmalonic acid chloride (prepared from tert-butyl phenyl malonic acid in benzene plus oxalyl chloride and a trace of dimethylformamide [DMF] in acetone). After 10 minutes at 0°–5° C. and one and one-half hours at room temperature, the reaction mixture was re-cooled to 0° C. to 5° C. and a few drops of water was added. After ten minutes this minute was evaporated under reduced pressure to dryness, the residue was taken up in ethyl acetate, the ethyl acetate solution was washed twice with cold 5 percent hydrochloric acid, with saturated aqueous sodium bicarbonate solution, with saturated aqueous sodium chloride solution, and then dried over magnesium sulfate, filtered and evaporated under reduced pressure. The oily tert-butyl 3-(2'-tert-butoxycarbonylvinyl)-7-(2'-tert-butoxycarbonyl-2'-phenylacetamido)-3-cephem-4-carboxylate ester was chromatographed over silica gel 15 percent water and eluted with 2 percent ethyl acetate in benzene. This title ester material crystallized from ethyl ether in the cold, m.p. 168°–170° C. and was characterized by IR, UV [λmax = 317 inμ (ε = 23,000)] and by elemental analysis which follows.

Analysis, Calc.: C, 61.98; H, 6.71; N, 4.66.
Found: C, 62.12; H, 6.90; N, 4.72.

EXAMPLE 7

3-(2'-carboxyvinyl-7-phenoxyacetamido)-3-cephem-4-carboxylic acid

A solution of 350 mg. of oily tert-butyl 3-(2'-tert-butoxycarbonylvinyl)-7-phenoxyacetamido-3-cephem-4-carboxylate, prepared by reacting (tert-butoxycarbonylmethylene)-triphenylphosphorane with tert-butyl 3-formyl-7-phenoxyacetamido-3-cephem-4-carboxylate-1-oxide and then reducing the sulfoxide, was stirred in 20 cc. of 98–100 percent formic acid for five hours at room temperature. The formic acid was removed under reduced pressure, and the residue was taken up in ethyl acetate. The title acid was separated by extraction of the ethyl acetate solution with aqueous sodium bicarbonate solution and then taken back into ethyl acetate by adding 20 percent hydrochloric acid. There was isolated 138 mg. of the title acid which could be crystallized from ethyl ether, m.p., 149°–151° C., and was characterized by IR, UV [λmax = 319 mμ (ε = 20,000)] and elemental analysis which follows:

Analysis, Calc.: C, 53.47; H, 3.99; N, 6.93.
Found: C, 53.52; H, 4.21; N, 6.72.

EXAMPLE 8

7-amino-3-(2'-carboxyvinyl)-3-cephem-4-carboxylic acid

A solution of 185 mg. of tert-butyl 7-amino-3-(2'-tert-butoxycarbonylvinyl)-3-cephem-4-carboxylate-p-toluenesulfonate in 20 ml. of 98–100 percent formic acid was stirred at room temperature for about 1 hour. The formic acid was removed under reduced pressure and after purging once with ethyl acetate, the residue was taken up in ethyl acetate:water mixture. The pH of the mixture was adjusted to 7.8 with saturated sodium bicarbonate solution and the organic layer was removed. The aqueous portion was cooled in an ice bath and the pH was adjusted to 3.0 by adding 5 percent hydrochloric acid. The precipitate which formed during hydrochloric acid addition was collected, yielding 80 mg. of the title product. A sample of the product turned orange when heated to 240°–250° C. but did not melt up to 290° C. The spectral data, IR, UV [λmax = 313 mμ (ε = 17,450)] and elemental analysis were consistent with the assigned structure:

Analysis, Calc.: C, 44.44; H, 3.73; N, 10.37.
Found: C, 44.70; H, 3.96; N, 10.10

EXAMPLE 9

3-(2'-ethoxycarbonylvinyl)-7-(2'-thienylacetamido)-3-cephem-4-carboxylic acid

To a cooled (0°–5° C.) solution of 210 mg. of tert-butyl 7-amino-3-(2'-ethoxycarbonylvinyl)-3-cephem-4-carboxylate-p-toluenesulfonate and 126 mg. (1.5 mmoles) of sodium bicarbonate, there was added 1.5 equivalents of freshly distilled 2-thienylacetyl chloride. After 30 minutes at 0° C. to 5° C. and two hours at room temperature, and re-cooling to 0° C. to 5° C. of the mixture, a small amount of water was added. After five minutes the reaction mixture was poured into ethyl acetate and washed twice with saturated aqueous sodium chloride solution, twice with cold 5 percent hydrochloric acid, three times with saturated aqueous sodium bicarbonate solution, once with saturated aqueous sodium chloride solution, dried over magnesium sulfate, filtered, and the solvent was removed under reduced pressure to leave as residue 146 mg. of tert-butyl 3-(2'-ethoxycarbonylvinyl)-7-[(2'-thienyl)acetamido]-3-cephem-4-carboxylate as a colorless oil.

The tert-butyl ester group was cleaved by dissolving the above oil in 10 cc. of 98–100 percent formic acid for 1.75 hours. After evaporating the formic acid under reduced pressure to dryness the title acid crystallized from ethyl ether, m.p., 191°–193° C. The structure was confirmed by IR, UV spectral analyses, and elemental analysis:

Analysis, Calc.: C, 51.19; H, 4.30; N, 6.63.
Found: C, 51.15; H, 4.44; N, 6.55.

EXAMPLE 10

7-AMINO-3-(2'-ethoxycarbonylvinyl)-3-cephem-4-carboxylic acid

A solution of 175 mg. of tert-butyl 7-amino-3-(2'-ethoxycarbonylvinyl)-3-cephem-4-carboxylate-p-toluenesulfonate in 20 ml. of 98–100 percent formic acid was stirred at room temperature for two hours. The excess formic acid was removed under reduced pressure and the residue was purged once with ethyl acetate and then taken up in ethyl acetate:water mixture. The pH of the mixture was adjusted to 8.0 with saturated sodium bicarbonate solution and the organic layer was separated and removed. The aqueous portion was cooled in an ice bath and the pH was adjusted to 3.5 with 5 percent hydrochloric acid. The precipitate which formed upon acid addition was collected, yielding 67 mg. of the title compound. It had a m.p. of 234°–237° C. (d), and the IR, UV [λmax. 324 mμ (ε = 14,800)] and elemental analysis were consistent with the assigned structure:

Analysis, Calc.: C, 48.32; H, 4.73; N, 9.39.
Found: C, 48.46; H, 5.01; N, 9.36.

EXAMPLE 11

3-(2'-ethoxycarbonylvinyl)-7-(2'-hydroxy-2'-phenylacetamido)-3-cephem-4-carboxylic acid Following the general procedure of Example 9, a salt of tert-butyl 7-amino-3-(2'-ethoxycarbonylvinyl)-3-cephem-4-carboxylate was acylated with the acid chloride derivative of 2-hydroxy-2-phenylacetic acid (mandelic acid), and after ester group removal the title compound was obtained as product.

EXAMPLES 12–15

Following the general procedure of Example 9, the tert-butyl 7-amino-3-(2'-ethoxycarbonylvinyl)-3-cephem-4-carboxylate ester salt was acylated with reactive variants of the respective acids, the tert-butyl ester groups were removed to obtain as products the following compounds: 3-(2'-ethoxycarbonylvinyl)-7-phenylacetamido-3-cephem-4-carboxylic acid; 3-(2'-ethoxycarbonylvinyl)-7-[2'-(4''-nitrophenyl)acetamido]-3-cephem-4-carboxylic acid; 3-(2'-ethoxycarbonylvinyl)-7-cyanoacetamido-3-cephem-4-carboxylic acid; 3-(2'-ethoxycarbonylvinyl)-7-(2'-carboxy-2'-phenylacetamido)-3-cephem-4-carboxylic acid.

EXAMPLE 16 tert-BUTYL 3-(2'-ethoxycarbonylvinyl)-7-(2'-CARBOXY-2'-phenylacetamido)-3-cephem-4-carboxylate Following the procedure of Example 9, the tert-butyl 7-amino-3-(2'-ethoxycarbonylvinyl)-3-cephem-4-carboxylate-p-toluenesulfonate ester salt was acylated with t-butyl phenylmalonic acid chloride to obtain thē title compound as product. The structure was confirmed by IR, UV and elemental analysis:

Analysis, Calc.: C, 60.82; H, 6.34; N, 4.89.
Found: C, 60.72; H, 6.62; N, 4.68.

EXAMPLE 17 tert-butyl 3-(2'-cyanovinyl)-7-phenoxyacetamido-3-cephem-4-carboxylate

To a solution of about 5.5 mmoles of the sulfoxide aldehyde[tert-butyl 3-formyl-7-phenoxyacetamido-3-cephem-4-carboxylate-1-oxide] in 50 cc. of a 1:1 v/v mixture of benzene and isopropanol there was added 5.5 mmoles of (cyanomethylene)-triphenylphosphorane. After stirring for 36 hours to insure complete reaction, the mixture was evaporated under reduced pressure to dryness, the residue was dissolved in 30 cc. of a 1:1 v/v dry DMF/acetonitrile mixture, the solution was cooled to 0°–5° C. and then 6 mmoles of potassium iodide and 2 cc. of acetyl chloride were added. After stirring the mixture for 10 minutes at (0°–5° C.) and 50 minutes at room temperature, the mixture was concentrated under reduced pressure, the residue was taken up in ethyl acetate and the solution was washed with saturated aqueous sodium chloride solution, with saturated aqueous sodium bicarbonate solution, with 10% w/v aqueous sodium thiosulfate solution, with saturated aqueous sodium chloride solution and then dried over magnesium sulfate, filtered and the solvents were removed under reduced pressure. The resulting title product was obtained as an oil. This oil was separated via a combination of column chromatography and preparative thin-layer chromatography techniques into the non-crystalline cis and trans isomers. These isomers had similar IR spectra but had different UV and NMR spectra. The significant spectral differences are given below.

Cis isomer

UV [λ max 317 mμ (ε = 16,800)]
NMR: vinyl H coupling constant = 12 Hz; C-2 H's as quartet, centered at 4.01δ

Trans isomer

UV [λ max 317 mμ (ε = 27,000)]
NMR: vinyl H coupling constant = 16 Hz; C-2 H's at singlet at 3.55δ

EXAMPLE 18 tert-butyl 3-(2'-ethoxycarbonylvinyl)-7-(2'-tert-butoxycarbonylamino-2'-phenylacetamido)-3-cephem-4-carboxylate To a cooled (0°–5° C.) solution of 160 mg. (0.3 mmoles) of tert-butyl 3-hydroxymethyl-7-(2'-tert-butoxycarbonylamino-2'-phenylacetamido)-3-cephem-4-carboxylate-1-oxide in 10 cc. of acetone there was added 10 drops of Jones reagent (solution of chromic acid and sulfuric acid in water). After one minute the reaction was quenched with isopropanol and aqueous sodium bicarbonate solution and poured into ethyl acetate. After washing the mixture with aqueous saturated sodium chloride solution, aqueous saturated sodium bicarbonate solution, aqueous saturated sodium chloride solution, drying over magnesium sulfate, and filtering, removal of the solvents under reduced pressure left as residue 174 mg. of the crude tert-butyl 3-formyl-7-(2'-tert-butoxycarbonylamino-2'-phenylacetamido)-3-cephem-4-carboxylate-1-oxide as a foam.

The above sulfoxide aldehyde ester foam was dissolved in 20 cc. of a 1:1 v/v isopropanol:benzene mixture and then 104 mg. (1 equivalent) of (carbethoxymethylene)-triphenylphosphorane was added. After stirring the mixture for 28 hours at room temperature, the mixture was evaporated under reduced pressure to dryness, the residue was dissolved in 8 cc. of a 1:1 v/v dry acetonitrile:DMF mixture and cooled to 0° C. to 5° C. To the cooled 0°–5° C. solution there was added 125 mg. (about 0.75 mmole) of potassium iodide and 0.6 cc. of acetyl chloride. The mixture was stirred 5 minutes at 0° C. to 5° C. and 1½ hours at room temperature. The mixture was evaporated under reduced pressure to dryness, the residue was taken up in ethyl acetate and washed with aqueous saturated sodium chloride solution, dried over magnesium sulfate and charcoal, filtered, and evaporated under reduced pressure to give 300 mg. of the crude product, named above. After purification by preparative thin-layer chromatography on silica gel, there was obtained 160 mg. of the above-titled product which crystallized from ethyl ether:cyclohexane mixture, m.p., 177°–179° C. The NMR, IR, UV [λ max=318 mμ (ε = 23,600)] spectral data were consistent with the assigned structure.

This compound is useful as an intermediate in the preparation of 3-(2'-ethoxycarbonylvinyl)-7-(2'-amino-2'-phenylacetamido)-3-cephem-4-carboxylic acid, a cephalosporin antibiotic.

EXAMPLE 19 tert-butyl 3-(2'-tert-butoxycarbonylvinyl)-7-(2'-tert-butoxycarbonylamino-2'-phenylacetamido)-3-cephem-4-carboxylate To a solution cooled to 0°–5° C. of 134 mg. (0.25 mmole) of tert-butyl 3-hydroxymethyl-7-(2'-tert-butoxycarbonylamino-2-phenylacetamido)-3-cephem-4-carboxylate-1-oxide in 10 cc. of acetone there was added nine drops of Jones reagent. After one minute the reaction mixture was quenched with isopropanol and sodium bicarbonate solution, poured into ethyl acetate and washed with saturated aqueous sodium chloride solution, with saturated aqueous sodium bicarbonate solution, with aqueous saturated sodium chloride solution, dried over magnesium sulfate, filtered and evaporated under reduced pressure to give as residue the crude sulfoxide aldehyde [tert-butyl 3-formyl-7-(2'-tert-butoxycarbonylamino-2-phenylacetamido)-3-cephem-4-carboxylate-1-oxide].

The above sulfoxide aldehyde ester was dissolved in 14 cc. of a 1:1 v/v isopropanol:benzene mixture and then 90 mg. (0.95 equivalent) of (tert-butoxycarbonylmethylene)-triphenylphosphorane was added. After being stirred for 24 hours at room temperature, the reaction mixture was evaporated under reduced pressure to dryness, the residue was taken up in 8 cc. of a 1:1 v/v dry acetonitrile:DMF mixture, cooled to 0° to 5° C. and then treated with 120 mg. of potassium iodide and 0.55 cc. of acetyl chloride. After 10 minutes at 0° C. to 5° C. and 50 minutes at room temperature, the reaction mixture was concentrated under reduced pressure, the residue was taken up in ethyl acetate, and washed with saturated aqueous sodium chloride solution, saturated aqueous sodium bicarbonate solution, 10% w/v aqueous sodium thiosulfate solution, saturated aqueous sodium chloride solution, dried over magnesium sulfate and charcoal, filtered, and the solvents were removed under reduced pressure to give 264 mg. of crude titled product.

This material was combined with the product from a similar reaction and chromatographed over silica gel — 15 percent water. The purified product, as titled above, crystallized from benzene, m.p., 197°-98° C. The IR, UV, and NMR spectra were consistent with the assigned structure for the titled compound:

Analysis, Calc.: C, 60.47; H, 6.71; N, 6.82.
Found: C, 60.72; H, 6.54; N, 6.77.

This compound is useful in the preparation of 3-(2'-carboxyvinyl)-7-(2'-amino-2'-phenylacetamido)-3-cephem-4-carboxylic acid, a cephalosporin antibiotic.

EXAMPLE 20

3-(2-cyanovinyl)-7-phenoxyacetamido-3-cephem-4-carboxylic acid

Each of the cis-and trans-isomers of tert-butyl 3-(2'-cyanovinyl)-7-phenoxyacetamido-3-cephem-4-carboxylate from Example 17 was in turn treated with 98–100 percent formic acid for 1 hour at room temperature to cleave the tert-butyl ester groups therefrom. After evaporation under reduced pressure of the excess formic acid, the acid residue was separated as an oil. Each product [the cis-or trans-isomer of the titled compound] showed a large antibiotic activity zone at 1 microgram/milliliter on a bioautograph test against B. subtilis.

The IR spectrum for each acid isomer was consistent with the assigned structure. The UV spectrum readings were:

cis: λ max 322 mµ (ε = 15,500)
trans: λ max 320 mµ (ε = 12,900)

Gradient plate antibiotic in vitro minimum inhibitory concentration (MIC) values indicated that the trans-isomer compound was more active than the cis-isomer against both Gram positive and Gram negative microorganisms.

EXAMPLE 21

7-(2'-carboxy-2'-phenylacetamido)-3-(2'-ethoxycarbonylvinyl)-3-cephem-4-carboxylic acid A solution of 23 mg. of tert-butyl 7-[2'-tert-butoxycarbonyl-2'-phenylacetamido]-3-(2'-ethoxycarbonylvinyl)-3-cephem-4-carboxylate, prepared as described in Example 16, in 10 cc. of 98–100 percent formic acid was allowed to stand for 1 hour at room temperature. The formic acid was removed under reduced pressure. The residue (the titled product) was purged of residual formic acid by dissolving in ethyl acetate and evaporating to dryness and then dissolved in aqueous sodium bicarbonate solution to make a water soluble sodium salt for biological evaluation.

EXAMPLE 22

7-(2'-carboxy-2'-phenylacetamido)-3-(2'-carboxyvinyl)-3-cephem-4-carboxylic acid In a manner similar to the procedure described in Example 21, the titled acid compound was prepared from tert-butyl 7-(2'-tert-butoxycarbonyl-2'-phenylacetamido)-3-(2'-tert-butoxycarbonylvinyl)-3-cephem-4-carboxylate, which ester was prepared by acylating tert-butyl 7-amino-3-(2'-tert-butoxycarbonylvinyl)-3-cephem-4-carboxylate-p-toluene sulfonate as described in Example 6.

EXAMPLE 23

7-(2'-amino-2'-phenylacetamido)-3-(2'-carboxyvinyl)-3-cephem-4-carboxylic acid

A solution of 25 mg. of tert-butyl 7-(2'-tert-butoxycarbonylamino-2'-phenylacetamido)-3-(2'-tert-butoxycarbonylvinyl)-3-cephem-4-carboxylate, prepared as described in Example 19, in 5 cc of 98–100 percent formic acid was allowed to stand for 1 hour at room temperature. After evaporating under reduced pressure the formic acid, the acid residue was taken up in trifluoroacetic acid and the NMR spectrum was taken. The trifluoroacetic acid was removed under reduced pressure and the acid residue showed a β-lactam in the IR spectrum and an acceptable UV [λ max.=317 mµ (ε = 13,700)]. The bioautograph showed only one antibiotically active zone against Sarcina lutea, which was more polar than cephalexin. Disc plate assay procedures showed antibiotic activity against a variety of Gram positive and Gram negative microorganisms.

EXAMPLE 24

7-(2'-amino-2'-phenylacetamido)-3-(2'-ethoxycarbonylvinyl)-3-cephem-4-carboxylic acid Following the procedure of Example 23, the titled acid compound was prepared from tert-butyl 7-(2'-tert-butoxycarbonylamino)-3-(2'-ethoxycarbonylvinyl)-3-cephem-4-carboxylate, which had been prepared as described in Example 18.

EXAMPLE 25

This example illustrates some of the antibiotic activity of a few examples of compounds of this invention. The data which follow are minimum inhibitory concentrations (MIC) in micrograms of compound per milliliter of agar medium in standard gradient plate in vitro tests against various Gram positive and Gram negative microorganisms. The data given here are for compounds satisfying the general formula $$R-\overset{O}{\overset{\|}{C}}-NH-CH-\overset{}{\underset{\underset{O}{\overset{\|}{C}}-N}{CH}}\overset{S}{\underset{\underset{COOH}{\overset{}{C}}}{\overset{}{\underset{}{\overset{}{\diagdown}}}}}\overset{CH_2}{\underset{C-CH=CH-X}{}}$$

where R and X are as defined in the table which follows:

TABLE

Gradient Plate In Vitro MIC's

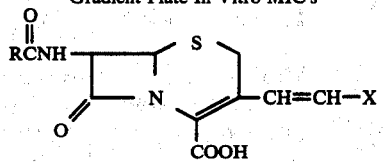

| | | G+ | | | | G- | | | | | |
|---|---|---|---|---|---|---|---|---|---|---|---|
| R | X | V41 | V32 | X400 | V84 | N9 | N10 | X26 | X68 | X514 | X528 | X99 |
| ⟨S⟩—CH₂— | CO₂Et | 6.2 | 7.5 | >20 | 7.1 | 2.6 | 3.8 | 5.3 | 3.3 | 4.7 | >50 | >50 |
| PhCH—<br>\|<br>COOH | CO₂Et | 7.9 | 10.3 | >20 | 11.4 | 1.0 | 6.3 | 2.5 | 3.0 | 0.8 | 42.2 | 0.6 |
| PhCH<br>\|<br>COOH | CO₂H | >20 | >20 | >20 | >20 | 7.0 | 36.5 | 35.0 | 2.0 | 1.0 | 29.5 | <8.0 |
| PhCH<br>\|<br>COOH | CN | 3.0 | 6.1 | >20 | 3.8 | 40.4 | 102.0 | 110.0 | 38.2 | 12.1 | 162.0 | 21.0 |
| D—PhCH<br>\|<br>OH | COOH | >20 | >20 | >20 | 11.2 | 3.3 | 5.7 | 5.0 | 1.0 | 0.6 | >50 | >50 |

TABLE footnotes:
1. The gradient plate procedure used is essentially thatdescribed by Bryson and Szybalski in 1952 (Science, 116, pp. 45–46). The inoculum treatment method used for penicillin-resistant Staphylococci was reported by Godzeski et al. in Antimicrobial Agents and Chemotherapy, May, 1961, pp. 547–554.
2. Gram positive microorganism identifications are all penicillin-resistant Staphylococcus aureus strains V-41, V-32, X-400, V-84. X-400 is also Methicillin-resistant.
3. Gram negative microorganism identifications:
N-9 is Schigella sp.
N-10 is Escherichia coli
X-26 is Klebsiella pneumonia
X-68 is Enterobacter aerogenes
X-514 is Salmonella heidellberg
X-528 is Pseudomonas aerogenosa
X-99 is Serratia marcescens

EXAMPLE 26

3-(2'-carboxyvinyl)-7-(sydnone-3-acetamido)-3-cephem-4-carboxylic acid tert-Butyl 7-amino-3-(2'-tert-butoxycarbonylvinyl)-3-cephem-4-carboxylate-p-toluenesulfonic acid salt, prepared as described in Example 5, is treated with sydnone-3-acetyl chloride to form the tert-butyl 3-(2'-tert-butoxycarbonylvinyl)-7-(sydnone-3-acetamido)-3-cephem-4-carboxylate ester. This ester is treated with 98–100 percent formic acid to remove tert-butyl and the tert-butoxycarbonyl group to form the title compound which is useful as an antibiotic.

EXAMPLE 27

3-(2'-ethoxycarbonylvinyl)-7-(1H-tetrazolyl-5-ylacetamido)-3-cephem-4-carboxylic acid tert-Butyl 7-amino-3-(2'-carboethoxyvinyl)-3-cephem-4-carboxylate p-toluenesulfonate is treated with 1H-tetrazol-5-ylacetylchloride to form tert-butyl-7-(1H-tetrazol-5-acetamido)-3-(2'-ethoxycarbonylvinyl)-3-cephem-4-carboxylate. Treatment of this compound with formic acid to remove the ester group gives the title compound.

EXAMPLE 28

A. benzhydryl 7-acetamido-3-hydroxymethyl-3-cephem-4-carboxylate

A starting material, 7-amino-3-hydroxymethyl-3-cephem-4-carboxylic acid, was prepared by treating 3-acetoxymethyl-7amino-3-cephem-4-carboxylic acid (7-ACA) with B.subtilis esterase by known procedures. To a stirred cooled (0°–5° C.) solution containing 35 g. of 7-amino-3-hydroxymethyl-3-cephem-4-carboxylic acid suspended in 24 ml. of water (pH about 2.5) there was added a portion of 75 ml. of cold 2N sodium hydroxide solution to adjust the pH to about 8.0. Ketene was bubbled into the reaction mixture and the pH was kept between 7.5 and 8.5 with the remaining 2N sodium hydroxide solution. When all of the 2N sodium hydroxide was added, ketene was added until the pH dropped to 5.5. The mixture was poured into 1 liter of cold (0°–5° C.) 20 percent v/v acetone in ethyl acetate and then enough cold (0°–5° C.) 6N hydrochloric acid solution was added to adjust the pH to about 2.0. The acidified solution was then poured into anhydrous sodium sulfate (Na₂SO₄) and thoroughly mixed. The acetone/ethyl acetate solution was decanted from the solid and filtered through more anhydrous sodium sulfate into a flask containing 24 g. of diphenyldiazomethane. The aqueous portion was extracted with five 600 ml. portions of cold 20 percent v/v acetone in ethyl acetate mixture, and each portion was in turn decanted and filtered into the flask containing the diphenyldiazomethane. The mixture was concentrated under reduced pressure to about 300 ml. and 1 liter of diethyl ether was added while stirring. The precipitate was collected yielding 30.9 g. of the titled product, m.p. 153°–154° C., whose NMR, IR, UV spectra were consistent with the assigned structure.

| Elemental Analysis for | Percent | | | |
|---|---|---|---|---|
| the Title Compound: | C | H | N | S |
| Calculated | 63.14 | 4.84 | 6.40 | 7.33 |
| Found | 62.84 | 5.06 | 6.39 | 7.43 |

B. benzhydryl 7-acetamido-3-(2'-methoxycarbonylvinyl)-3-cephem-4-carboxylate To a stirred cooled (0°–5° C.) solution containing 220 mg. of benzhydryl 7-acetamido-3-hydroxymethyl-3-cephem-4-carboxylate dissolved in 10 ml. of dry acetone there was added 15 drops of Jones reagent. The mixture was stirred at 0°–5° C. for 1 minute and then quenched with isopropanol and a small amount of saturated sodium bicarbonate solution. Ethyl acetate was added and the resulting solution was washed with saturated aqueous sodium chloride solution, saturated aqueous sodium bicarbonate solution, saturated aqueous sodium chloride solution again, dried over magnesium sulfate, filtered and evaporated under reduced pressure to give 225 mg. of benzhydryl 7-acetamido-3-formyl-3-cephem-4-carboxylate (one spot on a thin layer chromatogram). This aldehyde material was dissolved in a mixture of 10 ml. of dry benzene and 10 ml. of isopropanol. Then 1 equivalent of (carbmethoxymethylene)-triphenylphosphorane was added as a solid. The mixture was stirred for 1 hour at room temperature, evaporated under reduced pressure to dryness, taken up in ethyl acetate and washed with cold 5 percent v/v hydrochloric acid solution, saturated aqueous sodium bicarbonate solution, saturated aqueous sodium chloride solution, dried over magnesium sulfate, filtered and evaporated to give 293 mg. of the crude titled product mixed with triphenylphosphine oxide bi-product. When the crude product was applied to two commercially available preparative thin layer chromatography plates (solvent, 1:1 v/v ethyl acetate:benzene), there was obtained 90 mg. of the purified titled product whose NMR, IR and UV spectra were consistent with the assigned structure.

EXAMPLE 29

A. benzhydryl 7-acetamido-3-hydroxymethyl-3-cephem-4-carboxylate-1-oxide

To a stirred, cooled (0°–5° C.) solution of 876 mg. of benzhydryl 7-acetamido-3-hydroxymethyl-3-cephem-4-carboxylate in a mixture of 40 ml. of methylene chloride and 20 ml. of isopropanol there was added dropwise 407 mg. (equivalent, about 85% pure) of m-chloroperbenzoic acid in 20 ml. of isopropanol, During the addition a precipitate was formed which was collected and washed with ethyl acetate yielding 800 mg. of the titled compound, m.p. 178°–179° C. The NMR, IR, and UV spectra were consistent with the assigned structure.

B. benzhydryl 7-acetamido-3-(2'-ethoxycarbonylvinyl)-3-cephem-4-carboxylate To a stirred cooled (20° C.) solution containing 1.824 g. of benzhydryl 7-acetamido-3-hydroxymethyl-3-cephem-4-carboxylate-1-oxide dissolved in 35 ml. of dry dimethylformamide (DMF) mixed with 150 ml. of dry acetone there was added dropwise 4.5 ml. of Jones reagent. After stirring the mixture at 20° C. for 10 minutes the volume was reduced in vacuo to approximately one-half of the original volume, quenched with isopropanol, and poured into 100 ml. of ethyl acetate plus 100 ml. of saturated aqueous sodium chloride solution. The organic layer was separated and then washed successively with saturated aqueous sodium chloride solution, saturated aqueous sodium bicarbonate solution, saturated aqueous sodium chloride solution again and then dried over magnesium sulfate, filtered and evaporated to obtain benzhydryl 7-acetamido-3-formyl-3-cephem-4-carboxylate-1-oxide as an oil. The oil was dissolved in a mixture of 75 ml. of ethanol and 75 ml. of dry benzene. Then 1.39 g. of (carbethoxymethylene)-triphenylphosphorane was added as a solid with stirring. The mixture was stirred at room temperature for 1.5 hours, evaporated under reduced pressure and was purged with ethyl acetate and evaporated under reduced pressure to an oil. This material was then dissolved in 20 ml. of a mixture of 10 ml. of dry DMF and 10 ml. of dry acetonitrile, cooled to 0°–5° C., and then 1.976 g. of potassium iodide and 8 ml. of acetyl chloride was added. The mixture was stirred at 0°–5° C. for 5 minutes, and without cooling for 45 minutes, and evaporated under reduced pressure to an oil which was taken up in benzene. The benzene-oil mixture was washed successively with saturated aqueous sodium chloride solution, cold 5% hydrochloric acid solution, saturated aqueous sodium bicarbonate solution, 10% w/v aqueous sodium thiosulfate solution, saturated sodium chloride solution and then dried over magnesium sulfate. The solution was filtered, solvent removed under reduced pressure, and the residue was mixed with similar material and passed through a column containing 500 g. of silica gel (15% water) using a gradient elution technique with the product, benzhydryl 7-acetamido-3-(2'-ethoxycarbonylvinyl)-3-cephem-4-carboxylate coming off the column in a 12–17% ethyl acetate in benzene mixture. The product crystallized from a methylene chloride-ethyl ether mixture, m.p. 178°–179° C. The NMR, IR, and UV spectra were consistent with the assigned structure. The elemental analysis of the product was:

|  | %C | %H | %N |
|---|---|---|---|
| Calculated | 64.02 | 5.17 | 5.53 |
| Found | 64.32 | 5.37 | 5.23 |

Other useful antibiotic compounds or intermediate compounds of this invention include:

7-cyanoacetamido-3-(2'-carboxyvinyl)-3-cephem-4-carboxylic acid;

7-propionamido-3-(2'-propionoxycarbonylvinyl)-3-cephem-4-carboxylic acid;

7-octanamido-3-(2-cyanovinyl)-3-cephem-4-carboxylic acid;

7-(2'-chloroacetamido)-3-(2'-formylvinyl)-3-cephem-4-carboxylic acid;

7-(3'-bromopropionamido)-3-(2'-methoxyvinyl)-3-cephem-4-carboxylic acid;

7-(2'-azidoacetamido)-3-(2'-methylthiovinyl)-3-cephem-4-carboxylic acid;

7-(2',2'-dimethyl-2'-phenylacetamido)-3-(2'-carboxyvinyl)-3-cephem-4-carboxylic acid;

7-[2'-amino-2'-(2''-thienyl)acetamido]-3-(2'-propionoxycarbonylvinyl)-3-cephem-4-carboxylic acid;

7-[2'-hydroxy-2'-(3''-thienyl)acetamido]-3-(2'-nitrovinyl)-3-cephem-4-carboxylic acid;

7-[2'-amino-2'-(4''chlorophenyl)acetamido]-3-(2'-methylsulfonyl-vinyl)-3-cephem-4-carboxylic acid;

7-[2'-carboxy-2'-(3'', 4''-dichlorophenyl)acetamido]-3-(2'-propyl-sulfonylvinyl)-3-cephem-4-carboxylic acid;

7-[2'-(2''-thienyl)acetamido]-3-(2'-trifluoromethylvinyl)-3-cephem-4-carboxylic acid;

7-[2'-(2''-furyl)acetamido]-3-(2'-phenylvinyl)-3-cephem-4-carboxylic acid;

7-(1H-tetrazol-5-ylpropionamido)-3-[2'-(4''-bromophenyl)vinyl]-3-cephem-4-carboxylic acid;

7-[2'-carboxy-2'-(2''-thienyl)acetamido]-3-(2'-methoxyvinyl)-3-cephem-4-carboxylic acid;

7-(2'-cyano-2'-phenylacetamido)-3-(1'-octenyl)-3-cephem-4-carboxylic acid;

7-[2'-carboxy-2'-(3'', 4''-dichlorophenyl)acetamido]-3-(2'-(4''-nitrophenylvinyl)-3-cephem-4-carboxylic acid;

7-[2'-carbamyl-2'-phenylacetamido]-3-[2'-(3''-carbomethoxyphenyl) vinyl]-3-cephem-4-carboxylic acid;

7-[2'-Cyano-2'-(2'' -thienyl)acetamido]-3-[2'-(3''-butyl-thiophenyl)-vinyl]-3-cephem-4-carboxylic acid;

benzhydryl 7-[5'-acetamido-6'-carbomethoxyadipoylamido]-3-(2'-tert-butoxycarbonylvinyl)-3-cephem-4 carboxylate;

p-nitrobenzyl 7-succinimido-3-(1'-hexenyl)-3-cephem-4-carboxylate;

7-amino-3-(2'-nitrovinyl)-3-cephem-4-carboxylic acid-3,4 -dichlorobenzenesulfonic acid salt;

7-amino-3-(2'-propoxyvinyl)-3-cephem-4-carboxylic acid-p- chlorobenzenesulfonic acid salt;

7-amino-3-(2'-(4''-cyanophenyl)vinyl)-3-cephem-4-carboxylic acid-p-toluenesulfonic acid salt;

sodium 3-(2'-carboxyvinyl)-7-(2'-thienylacetamido)-3-cephem-4-carboxylate;

Potassium 3-(2'-Ethoxycarbonylvinyl)-7-(2'-amino-2'-phenylacetamido-3-cephem-4-carboxylate;

7-[2'-(3''-guanyl-1''-ureido)-2'-phenylacetamido]-3-carboxyvinyl)-3-cephem-4-carboxylic acid, 3-(Ethoxycarbonylvinyl)-7-[2'-N-sulfoamino-2'-(2''-thienyl)acetamido]-3-cephem-4-carboxylic acid, 3-(Ethoxycarbonylvinyl)-7-[2'-(3''-guanyl-1''-ureido)-2'-phenylacetamido]-3-cephem-4-carboxylic acid, 3-(4'-chlorophenylvinyl-7-[2'-N-sulfoamino-2'-(2-sydnone)-acetamido]-3-cephem-4-carboxylic acid, and the like.

EXAMPLE 30 benzhydryl 7-acetamido-3-(tert-butoxycarbonylvinyl)-3-cephem-4-carboxylate

In a manner similar to that described in Example 29, the titled compound of this example was prepared, and purified by column chromatography on silica gel — 15% water, and crystallized from ethyl ether, m.p. 109°-111° C. The structure was confirmed by spectral means.

I claim:

1. A compound of the formula

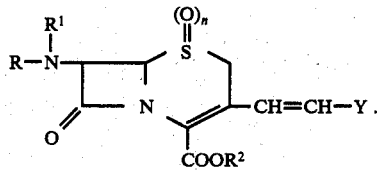

wherein
$n$ is 0 or 1;
R is hydrogen, cyanoacetyl or a group of the formula

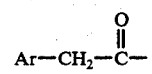

wherein Ar is 2-thienyl, 3-thienyl, 2-furyl, 3-furyl, 2-pyrrolyl, 3-pyrrolyl, phenyl, or nitrophenyl;

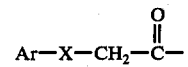

wherein X is oxygen or sulfur and Ar is as defined above;

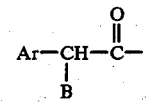

wherein Ar is as defined above and B is —OH, or such —OH group protected by esterification with a $C_1$-$C_6$ alkanoic acid; or
B is —COOH, or such —COOH group protected by esterification with a $C_1$-$C_6$ alkanol; or B is

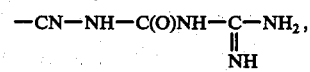

—NH-SO$_3$H, or —C(O)-NH$_2$;
R$^1$ is hydrogen, or
R and R$^1$ taken together with the nitrogen to which they are bonded denote —NH$_3^+$, a salt group with an acid having a pKa of less than 4, or a cyclic imide group from a $C_3$ to $C_{12}$ hydrocarbon dicarboxylic acid;
R$^2$ is hydrogen,
$C_4$ to $C_6$-tert-alkyl,
$C_5$ to $C_7$-tert-alkenyl,
$C_5$ to $C_7$-tert-alkynyl, or
a pharmaceutically acceptable cation; and
Y is —C(O)OR$^3$ where R$^3$ is $C_1$-$C_4$ alkyl, —CN, —COOH, —CHO, —X-$C_1$ to $C_4$ alkyl wherein X is oxygen or sulfur, —C(O)-NH$_2$, —NO$_2$, —S(O)-$C_1C_4$alkyl, —S(O)$_2C_1$-$C_4$alkyl, or Cl, Br, or trifluoromethyl.

2. A compound as defined in claim 1 wherein $n$ is 1; R is Ar-X-CH$_2$-c(o)—where X is —O— and Ar is phenyl, R$^1$ is hydrogen; R$^2$ is a $C_4$ to $C_6$-tert-alkyl; and Y is —CN, or —COO alkyl having from 1 to 4 carbon atoms in the alkyl groups.

3. A compound as defined in claim 2 wherein the compound is tert-butyl 3-(2'-ethoxycarbonylvinyl)-7-phenoxyacetamido-3-cephem-4-carboxylate-1-oxide.

4. A compound as defined in claim 1 wherein $n$ is O, R is selected from the group consisting of phenoxyacetyl, phenylacetyl,

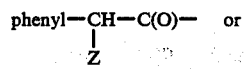

where in each of these formulas Z is hydrogen, —OH, —OH protected by esterification with a $C_1$ to $C_6$-alkanoic acid, —COOH, —COO-alkyl having from 1 to 6 carbon atoms in the alkyl, or Z is —CN, —C(O)NH$_2$, —NHSO$_3$H, or

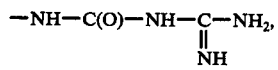

R$^1$ is hydrogen;
R$^2$ is C$_4$ to C$_6$-tert-alkyl; and
Y is —CN or —COO alkyl having from 1 to 4 carbon atoms in the alkyl.

5. A compound as defined in claim 4 wherein the compound is tert-butyl 3-(2'-ethoxycarbonylvinyl)-7-phenoxyacetamido-3-cephem-4-carboxylate.

6. A compound as defined in claim 1 wherein n is 0, each of R and R$^1$ is hydrogen, R$^2$ is a C$_4$ to C$_6$-tert-alkyl, and Y is selected from the group consisting of —CN, —COO alkyl having from 1 to 4 carbon atoms in each alkyl group, and salts of such compounds with an acid having a pKa of less than 4.

7. A compound as defined in claim 6 wherein the compound is alkylbenzenesulfonic acid salt of tert-butyl 7-amino-3-(2'-ethoxycarbonylvinyl)-3-cephem-4-carboxylate.

8. A compound as defined in claim 1 wherein n is 0, each of R and R$^1$ is hydrogen, R$^2$ is hydrogen, and Y is selected from the group consisting of —CN, —COOH, and —COO alkyl having from 1 to 4 carbon atoms in the alkyl.

9. A compound as defined in claim 1 wherein n is 0, R is selected from the group consisting of 2'-thienylacetyl, cyanoacetyl, a group of the formula

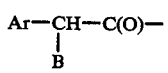

were Ar is -2-thienyl, phenyl, and B is —OH, —COOH, —CN, —C(O)NH$_2$,

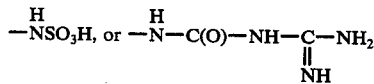

R$^1$ is hydrogen;
R$^2$ is hydrogen or a pharmaceutically acceptable cation;
Y is selected from the group consisting of —CN, —COOH, and —COO alkyl having from 1 to 4 carbon atoms in the alkyl group, and pharmaceutically acceptable salts thereof.

10. The compound of the formula

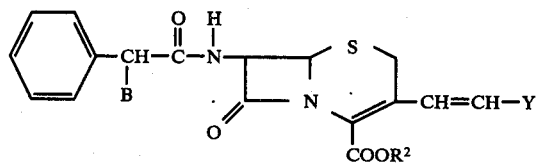

wherein B is hydroxy, formyloxy, carboxy, or t-butoxycarbonyl; Y is —CN, —COOH, or

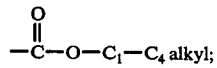

and R$^2$ is hydrogen, t-butyl, or a pharmaceutically acceptable cation.

11. A compound as defined in claim 10 wherein B is COOH and Y is —COOH or —C(O)OR$^3$.

12. A compound as defined in claim 10 wherein the compound is 3-(2'-ethoxycarbonylvinyl)-7-(2'-hydroxy-2'-phenylacetamido)-3-cephem-4-carboxylic acid.

13. A compound as defined in claim 11 wherein the compound is 3-(2'-ethoxycarbonylvinyl)-7-(2'-carboxy-2'-phenylacetamido)-3-cephem-4-carboxylic acid.

14. A compound as defined in claim 11 wherein the compound is 7-(2'-carboxy-2'-phenylacetamido)-3-(2'-carboxyvinyl)-3-cephem-4-carboxylic acid, sodium salt.

15. A compound as defined in claim 9 wherein the compound is 3-(2'ethoxycarbonylvinyl)-7-(2'-thienylacetamido)-3-cephem-4-carboxylic acid or a pharmaceutically acceptable salt thereof.

16. A compound as defined in claim 6 of the formula

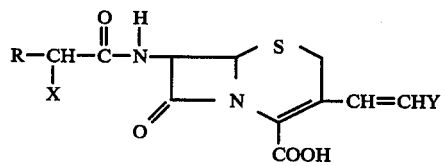

wherein R is phenyl; X is hydroxy, carboxy, or formyloxy; and Y is cyano, carboxy, or ethoxycarbonyl.

17. A compound of the formula

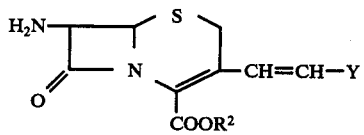

wherein R$^2$ is t-butyl and Y is t-butyloxycarbonyl, ethyloxycarbonyl, and cyano.

18. A compound of the formula

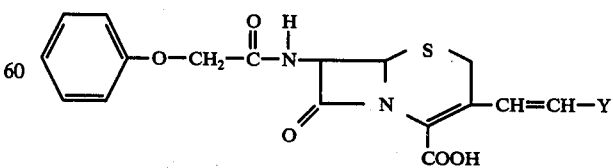

wherein Y is cyano, carboxy, or ethoxycarbonyl.

* * * * *